(12) United States Patent
Jimenez-Rios et al.

(10) Patent No.: US 9,297,499 B2
(45) Date of Patent: Mar. 29, 2016

(54) CRYOGENIC STORAGE CONTAINER, STORAGE DEVICE, AND METHODS OF USING THE SAME

(71) Applicant: Cook Medical Technologies LLC, Bloomington, IN (US)

(72) Inventors: Jorge L. Jimenez-Rios, Bloomington, IN (US); Bryan D. Woodard, Bloomington, IN (US); Shawn Nichols, Bloomington, IN (US); Scott K. Philhower, Bloomington, IL (US); Barry B. Hoult, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 258 days.

(21) Appl. No.: 14/097,357

(22) Filed: Dec. 5, 2013

(65) Prior Publication Data

US 2014/0157798 A1 Jun. 12, 2014

Related U.S. Application Data

(63) Continuation-in-part of application No. 14/077,707, filed on Nov. 12, 2013.

(60) Provisional application No. 61/735,194, filed on Dec. 10, 2012, provisional application No. 61/734,057, filed on Dec. 6, 2012.

(51) Int. Cl.
*F25D 25/00* (2006.01)
*F17C 13/00* (2006.01)
(Continued)

(52) U.S. Cl.
CPC ............ *F17C 13/001* (2013.01); *A01N 1/0257* (2013.01); *A01N 1/0268* (2013.01);
(Continued)

(58) Field of Classification Search
CPC ....... F25D 3/10; F25D 2331/804; F25D 3/08; B65D 81/3823
USPC ....................... 62/62, 371, 457.2, 457.5, 465; 220/560.12, 592.2
See application file for complete search history.

(56) References Cited

U.S. PATENT DOCUMENTS

| 129,094 A | 7/1872 | Briggs |
| 181,950 A | 9/1876 | Kromer |

(Continued)

FOREIGN PATENT DOCUMENTS

| FR | 2308068 | 4/1975 |
| FR | 2395780 | 1/1979 |

(Continued)

OTHER PUBLICATIONS

Patent Examination Report No. 1 for Australian Patent App. No. 2013356415, dated Sep. 4, 2015, 3 pp.
(Continued)

*Primary Examiner* — Melvin Jones
(74) *Attorney, Agent, or Firm* — Brinks Gilson & Lione

(57) ABSTRACT

A device for the cryopreservation and/or vitrification of a biological sample in a freezing medium is described. The device preferably comprises a bath for receiving a vessel containing a biological sample in liquid-phase nitrogen. In one example, the bath includes a first member extending generally vertically from a bottom wall portion which divides the interior chamber of the bath into a first sub-chamber adapted for receiving a volume of cryogenic freezing medium and a second or overflow sub-chamber adapted to receive freezing medium from the first sub-chamber. A second member extends generally horizontally between the sidewall portions of the bath and includes at least one opening for receiving a biological sample-containing vessel(s). A kit including a cryogenic storage device and a vessel is also described.

26 Claims, 8 Drawing Sheets

(51) Int. Cl.
*F25D 3/10* (2006.01)
*A01N 1/02* (2006.01)
*B01L 7/00* (2006.01)
*B01L 9/06* (2006.01)

(52) U.S. Cl.
CPC .. *B01L 7/50* (2013.01); *B01L 9/06* (2013.01); *F25D 3/10* (2013.01); *B01L 2200/147* (2013.01); *B01L 2300/1883* (2013.01)

(56) References Cited

U.S. PATENT DOCUMENTS

| | | | |
|---|---|---|---|
| 308,217 A | 11/1884 | Truxall | |
| 1,517,164 A | 11/1924 | Lear | |
| 1,763,461 A | 6/1930 | Fowler | |
| 2,315,425 A | 3/1943 | Hill et al. | |
| 3,092,974 A * | 6/1963 | Haumann | F17C 3/02 34/428 |
| 3,108,840 A | 10/1963 | Conrad et al. | |
| 3,168,362 A | 2/1965 | Perkins | |
| 4,377,077 A | 3/1983 | Granlund | |
| 4,390,111 A | 6/1983 | Robbins et al. | |
| 4,509,587 A | 4/1985 | Clark et al. | |
| 4,755,356 A | 7/1988 | Robbins et al. | |
| 4,859,610 A | 8/1989 | Maggio | |
| 4,874,102 A | 10/1989 | Jessop et al. | |
| 5,317,883 A * | 6/1994 | Newman | F25D 17/06 62/419 |
| 5,325,980 A | 7/1994 | Grimm et al. | |
| 5,382,409 A | 1/1995 | Baxter | |
| 5,711,446 A | 1/1998 | Jeffs et al. | |
| 5,850,917 A | 12/1998 | Denton et al. | |
| 5,894,733 A | 4/1999 | Brodner | |
| 5,916,525 A | 6/1999 | Husar et al. | |
| 6,047,845 A | 4/2000 | Rapaz | |
| 6,063,038 A | 5/2000 | Diamond et al. | |
| 6,065,294 A | 5/2000 | Hammerstedt et al. | |
| D427,691 S | 7/2000 | Asselta | |
| 6,701,743 B1 | 3/2004 | Durst et al. | |
| 6,805,842 B1 | 10/2004 | Bodner et al. | |
| 6,858,424 B2 | 2/2005 | Wisniewski | |
| 7,316,896 B2 | 1/2008 | Kuwayama et al. | |
| D630,478 S | 1/2011 | Zeller et al. | |
| 7,870,748 B2 | 1/2011 | Byrne | |
| 7,997,438 B2 | 8/2011 | Kelly | |
| 8,168,138 B2 | 5/2012 | Che et al. | |
| 8,177,123 B2 | 5/2012 | Voute et al. | |
| 2002/0162337 A1 * | 11/2002 | Peters | G01N 1/42 62/3.2 |
| 2006/0046243 A1 | 3/2006 | Stachecki et al. | |
| 2009/0019865 A1 * | 1/2009 | Henderson | A01N 1/00 62/62 |
| 2009/0120106 A1 | 5/2009 | Chin | |
| 2009/0123992 A1 | 5/2009 | Chin | |
| 2009/0123996 A1 | 5/2009 | Chin | |
| 2009/0186405 A1 | 7/2009 | Chin | |
| 2009/0255938 A1 | 10/2009 | Fuja | |
| 2010/0293970 A1 * | 11/2010 | Mooijer | F25D 16/00 62/62 |
| 2011/0120148 A1 | 5/2011 | Yoshimura et al. | |
| 2011/0129811 A1 | 6/2011 | Tao | |
| 2011/0150706 A1 | 6/2011 | Murphy et al. | |
| 2011/0239791 A1 | 10/2011 | Fici | |
| 2011/0275153 A1 | 11/2011 | Butler et al. | |
| 2012/0061392 A1 | 3/2012 | Beach et al. | |

FOREIGN PATENT DOCUMENTS

| | | |
|---|---|---|
| GB | 2407314 | 4/2005 |
| JP | 2001 252293 | 9/2001 |
| WO | WO 83/02386 | 1/1983 |
| WO | WO 2010/008083 A1 | 1/2010 |
| WO | WO 2012/158963 A2 | 11/2012 |

OTHER PUBLICATIONS

Chemglass Life Sciences, CLS-4758, Cryovials, Extra Long Lip Seal, Internal Thread with Silicone Washer, CLS-4758, http://www.chemglass.com/product_view.asp?pnr=CLS-4758, retrieved on Oct. 1, 2015, 2 pp.

"Cryovials & Accessories," (Chemglass Life Sciences) brochure, Feb. 1, 2010, XP055109581, Retrieved from the Internet: URL:http://chemglass.brookwood.com/pages/pdf/flyers/CryoVialBro_web.pdf [retrieved on Mar. 24, 2014] p. 2, 8 pages.

"Simport Micrewtubes | BioExpress Online," Nov. 26, 2012, Retrieved from the Internet: URL:http://web.archive.org/web/20121126034237/http://www.bioexpress.com/ divinity-cart/item/464300/SIMPORT-Micrewtubes/1.html? [retrieved on Mar. 24, 2014], 3 pages.

H. Chen et al, "The derivation of two additional human embryonic stem cell lines from day 3 embryos with low morphological scores," Human Reproduction, vol. 20, No. 8, pp. 2201-2206, 2005.

PCT International Search Report and Written Opinion for corresponding PCT/US2013/071589, mailed Apr. 7, 2014, 12 pages.

Patent Examination Report No. 1 for AU 2013355063 dated Jul. 23, 2015 (2 pages).

International Search Report and Written Opinion of the International Searching Authority for PCT/US2013/073539 dated Apr. 9, 2014 (10 pages).

International Preliminary Report on Patentability and Search Report for PCT/US2013/073539; dated Jun. 18, 2015, 7 pp.

* cited by examiner

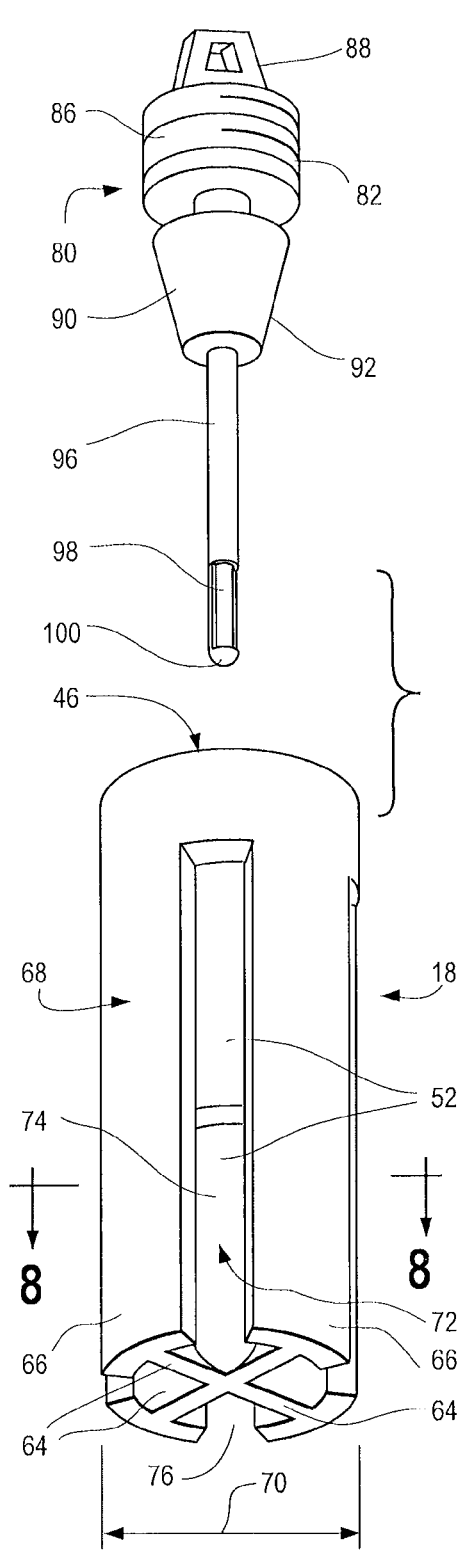
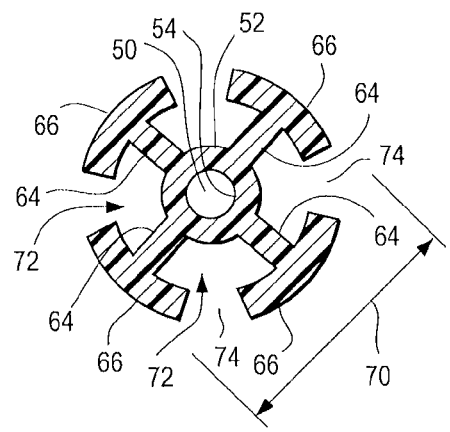
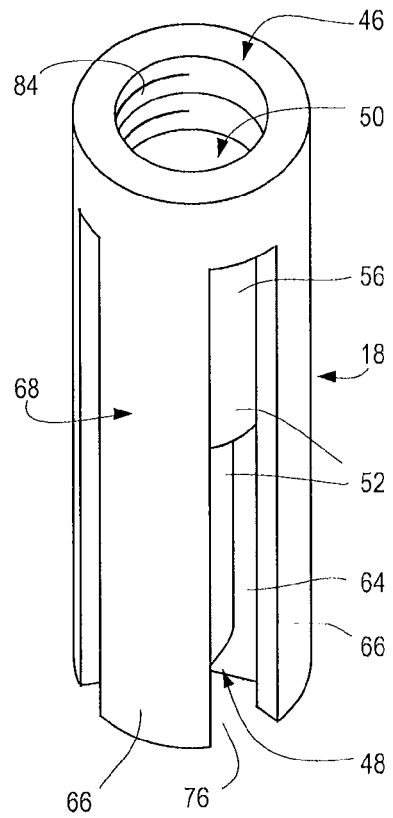
Fig. 7
Fig. 8
Fig. 9

Fig. 10
Fig. 11
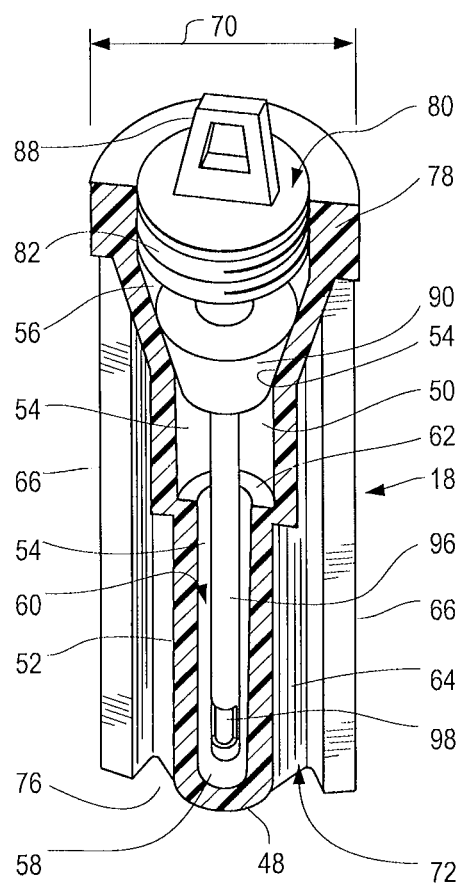
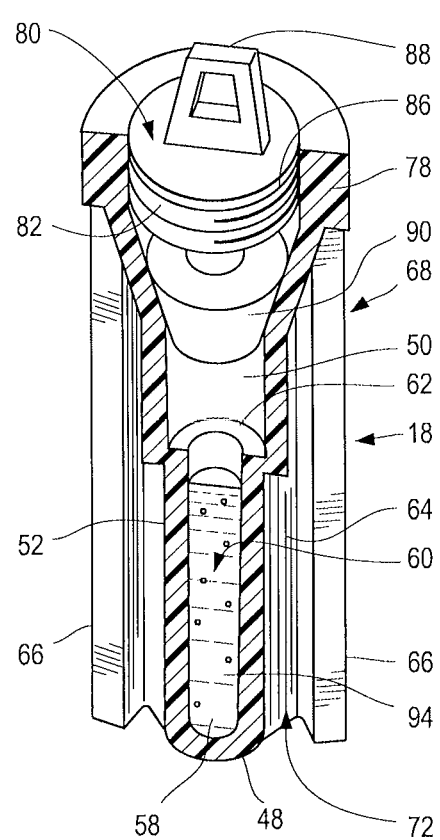

CRYOGENIC STORAGE CONTAINER, STORAGE DEVICE, AND METHODS OF USING THE SAME

RELATED APPLICATIONS

This application is a continuation-in-part of U.S. application Ser. No. 14/077,707 filed on Nov. 12, 2013 which claims the benefit of priority of U.S. Provisional application Ser. No. 61/734,057 filed on Dec. 6, 2012, and this application also claims the benefit priority of U.S. Provisional application Ser. No. 61/735,194, filed Dec. 10, 2012, which applications are incorporated by reference herein in their entireties.

TECHNICAL FIELD

The present invention relates generally to a device for the cryopreservation and/or vitrification of a biological sample in a freezing medium and more particularly, to a bath suitable for receiving and/or storing a container containing a biological sample in liquid-phase nitrogen.

There are a variety of applications in which it is desirable to preserve and store biological samples, including tissue cultures and cells, in a controlled environment. Various containers and storage methods have been investigated in order to maximize the viability of a particular stored sample while minimizing cost, hazards and handling difficulties. One particular situation in which specific containers and storage techniques are carefully selected and performed arises in cryobanking and assisted reproduction clinics and facilities. For example, such facilities may commonly use a device, sometimes referred to as a "bath" of cryogenic freezing medium, for the cryopreservation and/or vitrification and storage of sperm, oocytes and embryos.

Extremely cold temperatures are commonly used for the cryopreservation and vitrification of a particular biological sample. It is known to use liquid nitrogen vapors and/or liquid nitrogen or other suitable freezing media to achieve and maintain the extremely low temperature necessary to preserve the sample during cryopreservation and vitrification. Often, the biological sample is introduced into and held in container, such as a tube or vial, that is compatible with and able to withstand the high cooling rates and temperature ranges required for cryopreservation and vitrification. During conventional cryopreservation or "slow freeze", a biological specimen such as semen, contained within a vial, may be placed into a bath of suitable freezing media and chilled to a cryogenic storage temperature that is typically about −196 degrees C., the atmospheric boiling point of liquid nitrogen. Alternatively, during vitrification, a very small cellular sample such as an embryo, suspended in a droplet of vitrification preservation medium ("cryoprotectant") within a vial, is placed into a bath of freezing medium, which results in the sample becoming trapped in a glassy matrix (e.g. vitrified) within the vial.

When liquid nitrogen is used as the freezing medium for cryopreservation or vitrification of a particular sample, it may be desirable to submerge only a portion of the sample-containing vial into the liquid nitrogen bath. For example, the distal end portion of a vial (typically where the sample is held) may be submerged in order to maintain the sample at the desired cryogenic storage temperature, while the proximal end of the vial, including any cap or closure, may remain above the level of liquid nitrogen within the bath. Accordingly, it is desirable to provide a cryogenic storage device, such as a bath, which allows the level of liquid nitrogen in the bath to be easily and automatically regulated and maintained and also allows one or more sample-containing vials to be organized and held in a desired position and height relative to the level of liquid nitrogen within the bath for the cryopreservation and/or vitrification and storage of a biological sample.

SUMMARY

The present disclosure provides a cryogenic storage device. In one example, the device comprises a container comprising a bottom wall portion and a side wall portion which form an interior chamber and wherein the container comprises an inner surface and an outer surface. A thermal insulating material covers at least a portion of one or both of the inner and outer surfaces of the container. Preferably, a first member having a surface extending generally vertically from the bottom wall portion of the container divides the interior chamber into a first sub-chamber adapted for receiving a volume of cryogenic freezing medium and a second sub-chamber. The container further comprises a second member having a surface extending generally horizontally between the sidewall portions of the container, wherein the generally horizontal surface comprises at least one opening formed therein configured to receive one or more biological sample-containing vessels.

The present disclosure also provides cryogenic storage kit. In one example, the kit comprises a cryogenic storage device and a vessel. The vessel is preferably adapted to receive and retain a biological sample during cryopreservation. The cryogenic storage device may include a container comprising a bottom wall portion and a side wall portion that form an interior chamber and wherein the container comprises an inner surface and an outer surface. A thermal insulating material preferably covers at least a portion of one or both of the inner and outer surfaces of the container. A first member having a surface extending generally vertically from the bottom wall portion of the container divides the interior chamber into a first sub-chamber adapted for receiving a volume of cryogenic freezing medium and a second sub-chamber. A second member extends generally horizontally between the opposing sidewall portions of the container and preferably comprises at least one opening formed therein configured to receive one or more biological sample-containing vessels.

A cryogenic storage method is also disclosed. In one example, the method comprises introducing a biological sample into the lumen of a storage vessel and placing the storage vessel in a cryogenic storage device. In one non-limiting example, the storage device comprises a container comprising a bottom wall portion and at least two side wall portions, the bottom and side wall portions forming an interior chamber and wherein the container comprises an inner surface and an outer surface. A thermal insulating material covers at least a portion of one or both of the inner and outer surfaces of the container. A first member having extends generally vertically from the bottom wall portion of the container and divides the interior chamber into a first sub-chamber containing a volume of cryogenic freezing medium and a second sub-chamber, and a second member extends generally horizontally between the sidewall portions of the container into the first sub-chamber, wherein the generally horizontal surface comprises at least one opening formed therein configured to receive one or more biological sample-containing storage vessels. The method further comprises exposing at least a portion of the sample-containing vessel to a cryogenic freezing medium in the storage device.

BRIEF DESCRIPTION OF THE DRAWINGS

FIG. 7 is an exploded view of one example of a vessel or vial and a corresponding closure member that can be used with the cryogenic storage device described herein.

FIG. 8 is a cross-sectional view of the vessel shown in FIG. 7.

FIG. 9 is a top perspective view of the vessel shown in FIG. 7 with the closure member removed.

FIG. 10 is a side cross-sectional view of one example of a vessel and closure member that can be used with the cryogenic storage device described herein.

FIG. 11 is a side cross-sectional view of another example of a vessel and closure member that can be used with the cryogenic storage device described herein.

DETAILED DESCRIPTION

The examples and embodiments described below are primarily in connection with a device, such as a bath, suitable for the cryopreservation and vitrification of biological samples including sperm cells, oocytes and/or embryos and storage thereof in liquid-phase nitrogen. Also described is a sealable container suitable for the cryopreservation and vitrification of sperm cells, oocytes and/or embryos and storage thereof in liquid phase nitrogen, however, the described device and container may also be used in connection with a range of medical procedures and methods including the preservation and sealed storage of biological samples in a variety of environments and temperatures.

In the description that follows, reference will be made to cryopreservation and vitrification of biological samples. The terms "cryopreservation" and "vitrification" may be used interchangeably unless otherwise noted and, for simplicity, may simply be referred to by one term or the other.

Figure 1:
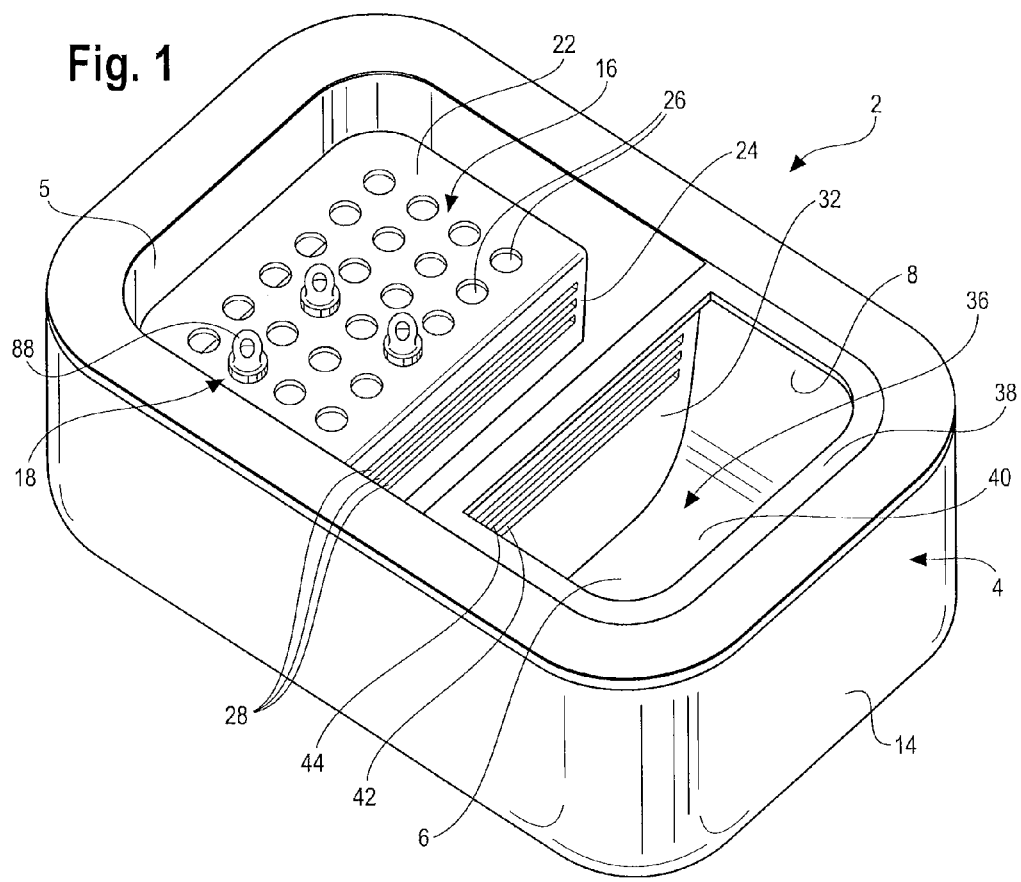
FIG. 1 is a perspective view of one example of a cryogenic storage device for the cryopreservation and/or vitrification and storage of a biological sample.
Figure 2:
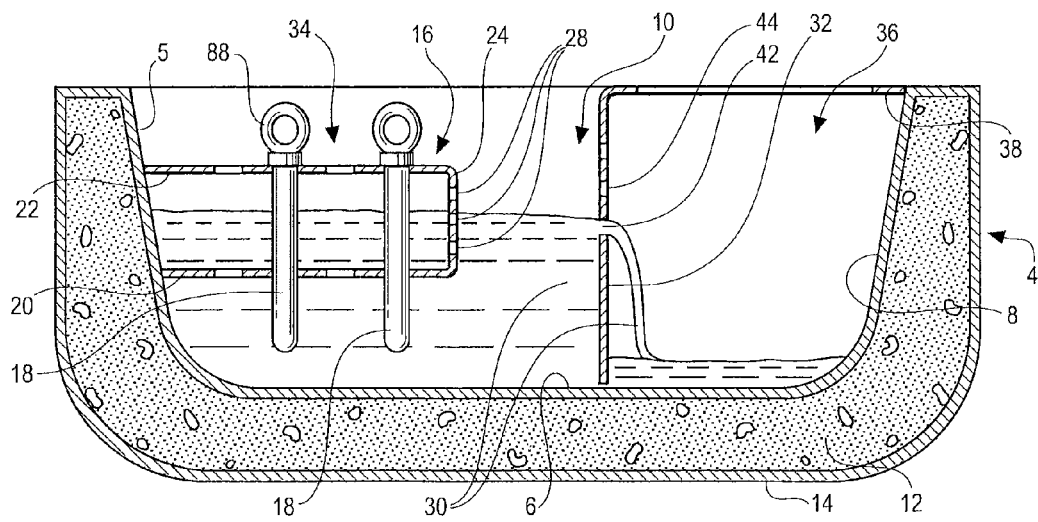
FIG. 2 is a side cross-sectional view of the cryogenic storage device illustrated in FIG. 1.
Figure 3:
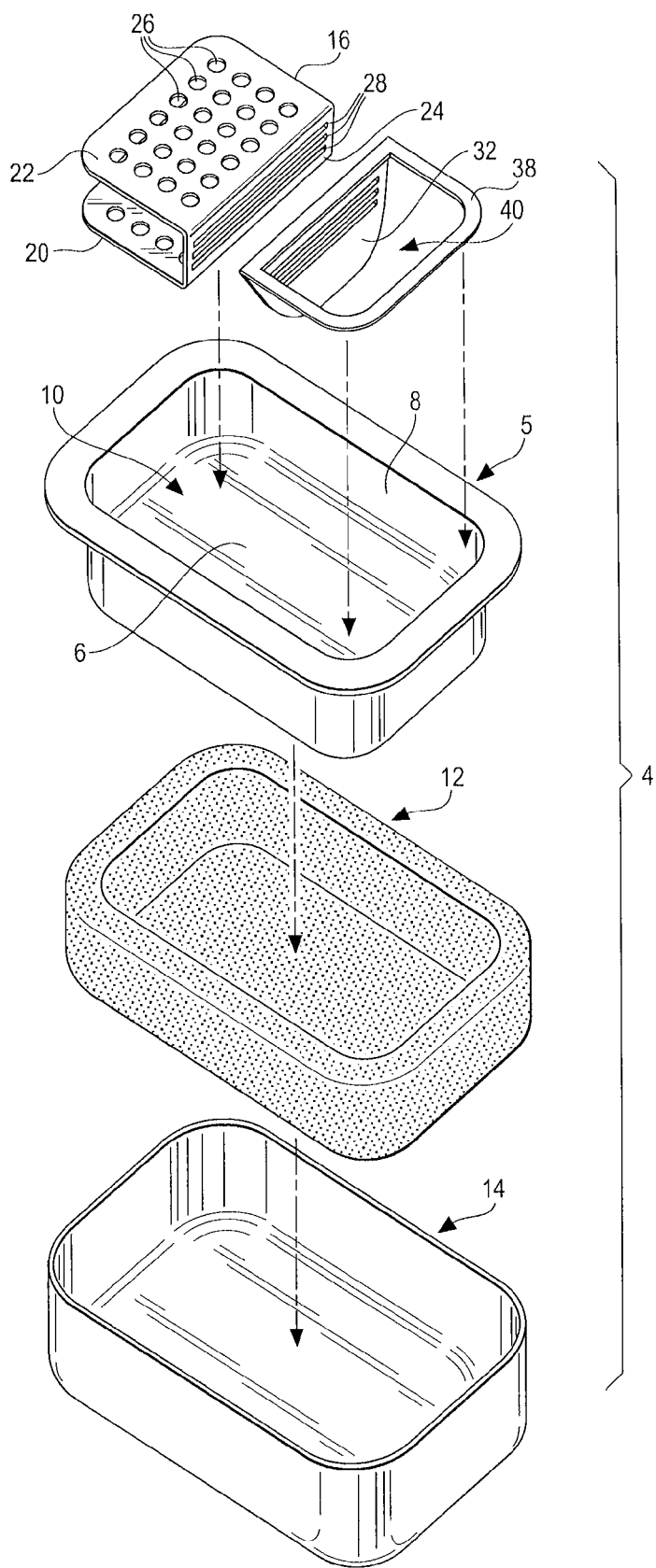
FIG. 3 is an exploded perspective view of one example of the various components of the cryogenic storage device illustrated in FIG. 1.

FIG. 1 illustrates one example of a device for receiving and storing a biological sample, identified generally at 2. The device 2 is preferably a container 4 suitable for use in the cryopreservation and/or vitrification and, if desired, the storage of biological samples. The device described herein may be referred to as a "bath" or "cryobath". In one non-limiting example, the biological sample may include oocytes, a semen sample containing many sperm cells and/or one or more embryos, but can also be applied to other cellular samples as will be apparent to those skilled in the art. As shown in FIGS. 1 and 2, the cryobath 4 may include a bottom wall portion 6 and a side wall portion 8 that together form an interior chamber 10. Preferably, the bath 4 has a generally bowl-shaped interior reservoir or container 5, but may be any number of suitable shapes and sizes as needed or required. In one particular example and as shown in FIGS. 2 and 3, the bath 4 is a stainless steel bowl-shaped reservoir 5 covered, at least in part, with a thermal insulating material 12, such as polystyrene foam. Alternatively, a layer of vacuum insulation or other acceptable materials and/or methods of maintaining the proper and desired temperature of the contents of reservoir may be provided in addition to and/or in place of thermal insulating material 12. The insulating material 12 may be further covered by an outer casing 14 made of plastic or metal. The various materials selected for the construction of the device, including the material of the interior bowl 5, insulation 12 and/or casing 14, is preferably capable of withstanding and maintaining the temperature ranges required for cryopreservation and vitrification. For example, the materials that make up one or more of the various layers of the bath 4 are adapted to receive and retain a cryogenic freezing medium (including, but not limited to liquid nitrogen) in the interior chamber 10 of the device without cracking, becoming brittle or otherwise deteriorating, deforming, or losing structural integrity.

As illustrated in FIGS. 1-3, the cryo bath 4 may preferably include a rack or organizer 16 for holding and organizing one or more vessels 18, such as cryo vials, tubes and/or straws, during cryopreservation and/or vitrification and storage of a biological sample held therein. The rack 16 may have a variety of configurations or designs that are suitable for receiving and holding one or more vials 18 including, but not limited to a plate, a support, a shelf, a cane and the like. The rack 16 may be secured to the interior chamber 10 of the bowl 5 such as by adhesive, welding, bonding and the like, or alternatively, the rack 16 may be removable such that it is snap-fitted, held by friction fit between the side wall portions 8 and/or otherwise removably held in place by one or more fasteners. An exemplary rack 16 is shown in FIG. 2 as a generally horizontal member that extends from the side wall portion 18 of the interior chamber 10 of the bath 4. More particularly, the rack 16 is a generally U-shaped member having a bottom portion 20 for holding or supporting the distal end of a vial 18, a top portion 22 for holding or supporting the proximal end or neck of a vial 18, and a vertical sidewall 24 extending between the top and bottom portions of the rack. One or more apertures 26 in the top 22 and/or bottom 20 portions of the rack 16 are configured to receive an individual vial 18 therein and hold the vial in a generally upright orientation. As shown in FIG. 2, the sidewall 24 of the rack preferably includes one or more openings or slots 28 to allow fluid, such as a cryogenic freezing medium 30 contained in the interior chamber 10 of the bath 4, to flow freely into and through the rack, thus also flowing freely around and between any vial(s) 18 that might be held in the rack 16. In this way, the cryogenic freezing medium 30, such as liquid nitrogen, may contact at least a portion of the outer surface of the vial(s), and in particular, the distal portion of a vial(s) that is submerged in the liquid nitrogen pool in the container interior chamber 10.

As further illustrated in FIGS. 1 and 2, the cryo bath 4 also preferably includes a member 32 that extends in a generally vertical direction from the bottom wall portion 6 of the interior chamber 10 of the bath. In one example, this generally vertical member 32 is a barrier such as a wall, a plate, a sheet, a membrane or the like, that divides the interior chamber 10 of the bath into at least a first sub-chamber 34 and a second sub-chamber 36. The barrier 32 may be secured to the interior chamber 10 of the bowl 5 such as by adhesive, welding, bonding or the like, or alternatively the barrier 32 may be removable, such that it is snap-fitted, held by friction fit and/or removably held in place by one or more fasteners. The barrier 32 may divide the bath into equally sized first and second sub-chambers 34, 36, or alternatively, the barrier may be positioned within the interior chamber 10 of the bath 4 such that one of the sub-chambers is larger than the other. The barrier 32 may also optionally include an upper horizontal lip 38 or wall which may be a solid surface or, as FIGS. 1 and 3 illustrate, may be in the form of a frame that defines an opening 40 and allows access into the interior of one of the sub-chambers. The lip 38 may help to secure the barrier 32 to one or more additional points along the side wall portion 8 of the interior chamber 10, thus providing additional stability to the barrier 32 and supplying reinforcement and/or support to the vertically orientated surface of the barrier 32. As FIGS. 1 and 2 illustrate, the vertically oriented portion of the barrier 32 preferably includes one or more openings or slots that provide fluid communication between the first and second sub-chambers 34, 36. Preferably, the vertical barrier 32 includes at least two horizontal elongated slots formed therein, including a lower-most slot 42 and a second slot 44 formed in the barrier above the lower-most slot 42. The barrier 32 may include additional openings or slots as necessary or desired.

As shown in FIG. 2, the rack 16 with one or more vials 18 arranged thereon may extend horizontally into the first sub-chamber 34 which may be filled with a cryogenic freezing medium 30 such as liquid nitrogen. When the level of liquid nitrogen 30 in the first sub-chamber 34 reaches the lower opening or slot 42 in the vertical barrier 32, the liquid nitrogen 30 may flow through the slot 42 and into the second sub-chamber 36. In this way, the second sub-chamber 36 serves as an "overflow" chamber for receiving a portion of the liquid nitrogen 30 or other cryogenic media or fluid from the first sub-chamber 34. As such, the volume of liquid nitrogen, and the maximum height or level to which the liquid nitrogen may fill the first sub-chamber 34, can be controlled by the position of the opening(s) in the vertical barrier 32. In other words, the maximum level of liquid nitrogen in the first sub-chamber 34 may only fill up to, and be maintained, as high as the vertical height of the lowest opening 42 in the barrier 32. If and when the liquid nitrogen 30 in the first sub-chamber 34 is filled to a level higher than the lowest opening 42, the nitrogen will immediately and automatically flow through the opening 42 and into the overflow sub-chamber 36.

In the event that the first sub-chamber 34 is filled very rapidly, the level of liquid nitrogen 30 may temporarily surpass the vertical level of the lower-most opening 42 in the barrier 32 and begin to flow through a second opening 44 located slightly above the lower-most opening in the barrier. As such, the second opening 44 in the barrier 32 provides a supplemental path for the flow of liquid nitrogen 30 from the first sub-chamber 34 to the second 36 in the event that the lowermost slot 42 is unable to accommodate the "overflow" volume of liquid nitrogen 30 from the first sub-chamber 34, such as what may occur when the first sub-chamber 34 is rapidly or abruptly overfilled with a volume of liquid nitrogen greater than the desired maximum level. At this point, liquid nitrogen 30 from the first sub-chamber 34 will flow through both openings 42 and 44 in the barrier 32 until the maximum level of liquid nitrogen in the first sub-chamber 34 recedes to a level below upper opening 44. Liquid nitrogen may continue to flow through the lower-most opening 42 in the barrier 32 until equilibrium is again achieved, or, in other words, until the maximum level or volume of liquid nitrogen in the first sub-chamber 34 has receded to a point where it is at least below the lower-most opening 42 in the barrier. The maximum level of liquid nitrogen in the first sub-chamber 34 can thus be controlled and maintained at a particular desired vertical height relative to the rack or organizer 16 as well as relative to the biological sample-containing vials 18 held thereon.

The maximum level of liquid nitrogen 30 in the first sub-chamber 34 can also be adjusted, as needed, in a number of ways. In one example, the height of the one or more openings/slots 42, 44 in the generally vertical barrier 32 can me moved higher (allowing the first sub-chamber 34 to accommodate a greater volume and higher maximum level of liquid nitrogen) or lower (thus reducing the volume and maximum level of liquid nitrogen that the first sub-chamber can accommodate). This could be accomplished by providing a different vertical barrier with slots arranged at a different height and simply removing the existing barrier and replacing it with another having slots at the different desired height. In addition, or in combination with the previously mentioned adjustment, the position of the rack 16 can also be adjusted so that the rack extends from the side wall 8 of the bath 4 at a point that is either higher or lower. Thus, any vial(s) 18 retained within the rack 16 may be more or less submerged, respectively, in the volume of liquid nitrogen 30 contained in the first sub-chamber 34 as the vertical position of the rack 16 is changed or adjusted. In addition, the overflow chamber may have a drain or opening at the bottom that releases the liquid nitrogen from the bath, such as to an outside catch tray, hose, tube, container or the like to recapture the liquid nitrogen for further use or for disposal.

Figure 14:
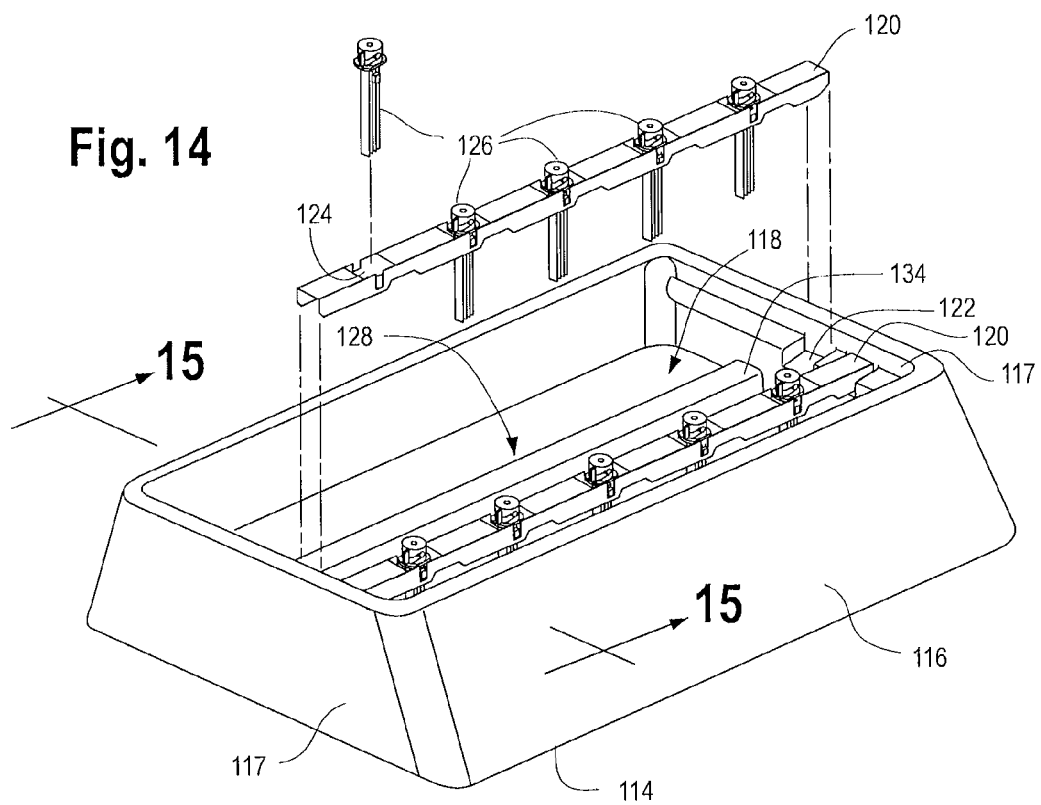
FIG. 14 is a perspective view of another example of a cryogenic storage device for the cryopreservation and/or vitrification and/or storage of a biological sample.
Figure 15:
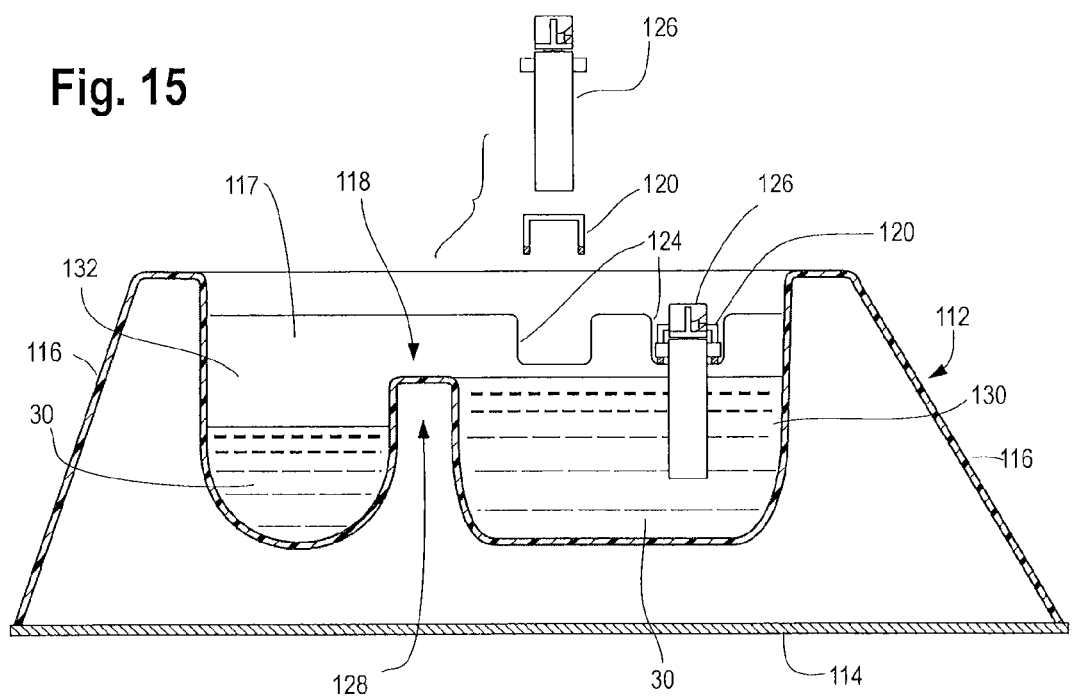
FIG. 15 is a side cross-sectional view of the cryogenic storage device illustrated in FIG. 14.

In another example, FIGS. 14 and 15 illustrate another example of a device for receiving and storing a biological sample, identified generally at 112. As described above in connection with FIGS. 1-3, the bath shown in FIGS. 14 and 15 may also include a bottom wall portion 114, two opposing side wall portions 116 and to opposing end wall portions 117 that together form an interior chamber 118. Preferably, the bath 112 has a generally bowl-shaped interior reservoir or chamber, but may be any number of suitable shapes and sizes as needed or required. In one particular example, the bath 112 is preferably a plastic and/or a stainless steel bowl-shaped reservoir that may be insulated, such as with a thermal insulating material and/or a layer of vacuum insulation. Other acceptable materials and/or methods of maintaining the proper and desired temperature of the contents of reservoir 118 may be provided. The various materials selected for the construction of the device 112, are preferably capable of withstanding and maintaining the high cooling rates and temperature ranges required for cryopreservation and vitrification. For example, the materials that make up one or more of the various layers of the bath 112 are adapted to receive and retain a cryogenic freezing medium (including, but not limited to liquid nitrogen) in the interior chamber 118 of the device without cracking, becoming brittle or otherwise deteriorating, deforming, or losing structural integrity.

As illustrated in FIGS. 14 and 15, the bath 112 may preferably include an organizer for holding and organizing one or more vessels 18, 126, such as cryo vials, tubes and/or straws, during cryopreservation and/or vitrification and storage of a biological sample held therein. The organizer may have a variety of configurations or designs that are suitable for receiving and holding one or more vials 18, 126 including, but not limited to a plate, a support, a shelf, and the like, and preferably, the organizer is a cane 120. The cane 120 may be secured to the interior chamber 118 of the bath 112 such as by adhesive, welding, bonding and the like, or alternatively, the cane 120 may be removable such that it is snap-fitted, held by fasteners, friction fit between the opposing end wall portions 117 and/or otherwise held in place by one or more indentations or notches 122 formed in the end wall 117 as shown in FIG. 14. An exemplary cane 120 is shown in FIG. 14 as a generally horizontal member that extends from one end wall 117 to the other end wall 117 of the bath 112. More particularly, the cane 120 is a generally linear member for receiving, holding or supporting a vial 18, 126. One or more apertures 124 formed in the cane 120 are configured to receive an individual vial 18, 126 therein and hold the vial in a generally upright orientation. In this way, the cryogenic freezing medium 30, such as liquid nitrogen, may contact at least a portion of the outer surface 68 of the vial(s) 18, 126, and in particular, the distal portion 48 of a vial(s) that is submerged in the liquid nitrogen pool in the container interior chamber 118.

As further illustrated in FIGS. 14 and 15, the cryo bath 112 also preferably includes a member 128 that extends upwards from the bottom wall portion 114 of the interior chamber 118 of the bath 112. In one example, this member 128 is a barrier, and as FIG. 15 shows, is a "bump" or protrusion extending upwards from the bottom wall 114 of the bath 112, but may also include a wall or similar structure, for example, that divides the interior chamber 118 of the bath 112 into at least a first sub-chamber 130 and a second sub-chamber 132. The barrier 128 may be removable, and secured to the interior chamber 118 such as by adhesive, welding, bonding or the like, or alternatively the barrier 128 may be integrally formed with the interior chamber 118 of the bath 112. The barrier 128 divides the bath 112 into equally sized first and second sub-chambers 130, 132, or alternatively, as FIG. 15 illustrates, the barrier may be positioned within the interior chamber 118 of the bath 112 such that one of the sub-chambers 130 is larger than the other 132.

The cane 120 with one or more vials 18, 126 arranged thereon may extend horizontally across the first sub-chamber 130 which may be filled with a cryogenic freezing medium 30 such as liquid nitrogen. When the level of liquid nitrogen 30 in the first sub-chamber 130 reaches the height of the top surface 134 of the vertical barrier 128, the liquid nitrogen 30 may flow over the top 134 of the barrier 128 and into the second sub-chamber 132. In this way, the second sub-chamber 132 serves as an "overflow" chamber for receiving a portion of the liquid nitrogen 30 or other cryogenic media or fluid from the first sub-chamber 130. As such, the volume of liquid nitrogen, and the maximum height or level to which the liquid nitrogen may fill the first sub-chamber 130 can be controlled by the height of the vertical barrier 128. In other words, the maximum level of liquid nitrogen 30 in the first sub-chamber 130 may only fill up to, and be maintained, as high as the vertical height of the top surface 134 of the barrier 128. If and when the liquid nitrogen 30 in the first sub-chamber 130 is filled to a level higher than the top surface 134 of the barrier 128, the liquid nitrogen will immediately and automatically flow over the barrier 128 and into the overflow sub-chamber 132. Liquid nitrogen 30 may continue to flow over the barrier 128 until equilibrium is again achieved, or, in other words, until the maximum level or volume of liquid nitrogen 30 in the first sub-chamber 130 has receded to a point where it is at least below the upper-most top surface 134 of the barrier 128. The maximum level of liquid nitrogen 30 in the first sub-chamber 130 can thus be controlled and maintained at a particular desired vertical height relative to the cane 120 as well as relative to the biological sample-containing vials 18, 126 held thereon.

The maximum level of liquid nitrogen 30 in the first sub-chamber 130 can also be adjusted, as needed, in a number of ways. In one example, the height of the barrier 128 can me moved higher (allowing the first sub-chamber 130 to accommodate a greater volume and higher maximum level of liquid nitrogen 30) or lower (thus reducing the volume and maximum level of liquid nitrogen 30 that the first sub-chamber 130 can accommodate). This could be accomplished by providing a different vertical barrier 128 with a different height. In addition, or in combination with the previously mentioned adjustment, the position of the cane 120 can also be adjusted at a point that is either higher or lower. Thus, any vial(s) 18, 126 retained within the cane 120 may be more or less submerged, respectively, in the volume of liquid nitrogen 30 contained in the first sub-chamber 130 as the vertical position of the cane 120 is changed or adjusted. In addition, the one or both of the chambers may have a drain or opening (not shown) at the bottom that releases the liquid nitrogen 30 from the bath 112, such as to an outside catch tray, hose, tube, container or the like to recapture the liquid nitrogen 30 for further use or for disposal.

Turning back now to FIGS. 1-3 and 14-15, and, as mentioned above, the rack 16 or cane 120 in the interior chamber 10, 118 of the bath 4, 112 is adapted to receive at least one biological sample-containing vessel such as cryo vial 18, 126. While particular examples of a vial are described in detail below, it is contemplated that a vessel or vial having a variety of shapes, sizes and dimensions may be used with the device 2, 112 described herein depending on numerous factors including the particular biological sample being handled, the techniques being performed and the desired outcome or objective.

Figure 12:
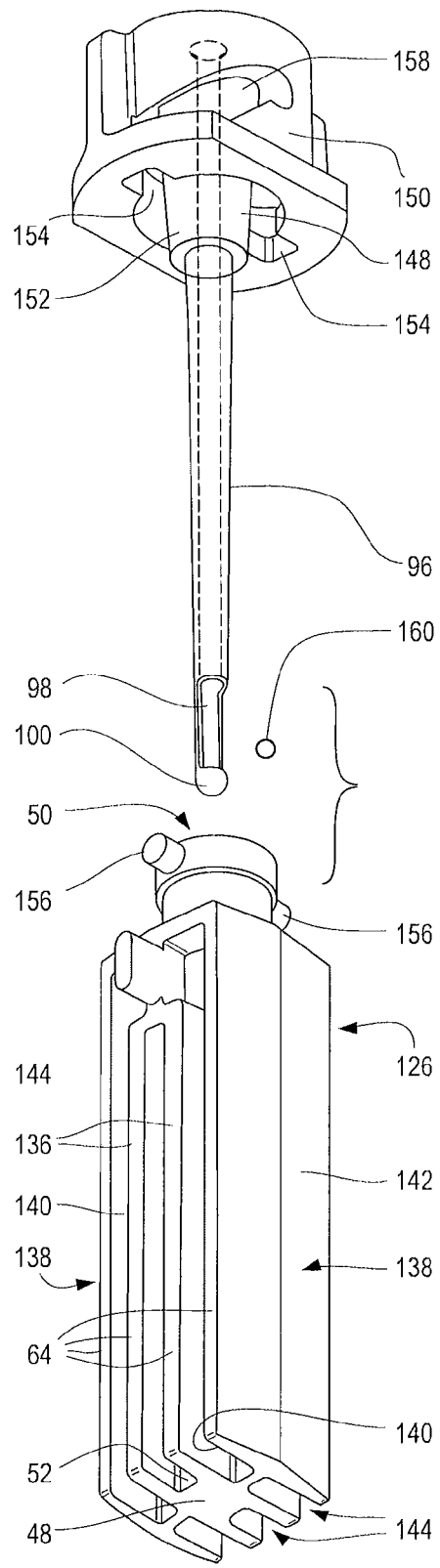
FIG. 12 is an exploded view of another example of a vessel or vial and a corresponding closure member that can be used with the cryogenic storage device described herein.
Figure 13:
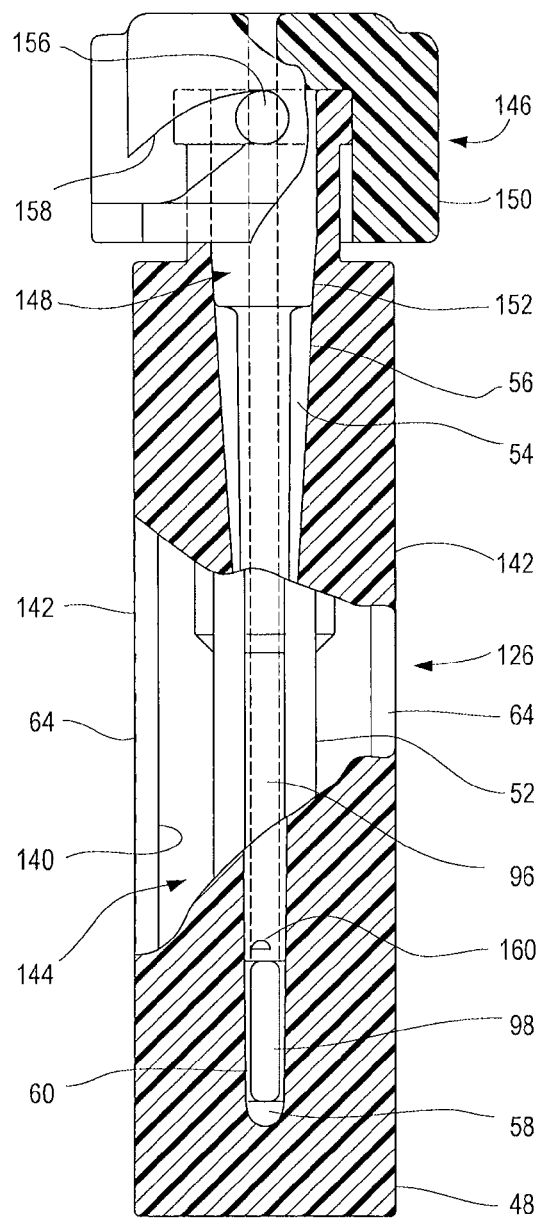
FIG. 13 is a partial cut-away side view and partial cross-sectional view of the vessel of FIG. 12.

In one example, as shown in exemplary FIGS. 7-11, and FIGS. 12-13, the vial 18, 126 includes an open proximal end 46 and a sealed distal end 48, with a lumen 50 extending between the respective ends. The lumen has an internal surface 54 and an external surface 52. In one example, the internal surface 54 has a variable diameter, and preferably, the internal surface of the lumen tapers radially inwardly from a wider 56 open proximal end 46 to a more narrow 58 sealed distal end 48, where a selected biological sample may be received 60 for cryopreservation or vitrification and held for storage. The taper may be gradual such that the lumen wall has a generally consistent taper angle between the proximal 46 and distal ends 48 as shown in FIG. 13 or, alternatively, the taper may be stepped as FIGS. 10 and 11 illustrate, where the lumen 50 is wider 56 near the proximal end and one or more shoulders or annular ledges 62 leads to a relatively more narrow 58 sample receiving portion 60 near the sealed distal end 48 of the lumen 50. In one non-limiting example, the internal lumen 50 can vary in diameter from about 2 mm at the more narrow diameter portion to about 7 mm at the wider diameter portion.

One or more protrusions or projections 64 may extend radially outwardly from the external surface 52 of the vial lumen 50. The projections 64 may be in the form of spokes, posts, wings, walls, panels, baffles or a combination thereof. The projections may be intermittently spaced or solid structures, and either integrally formed with the external surface 52 of the lumen wall or separately formed structures that are secured to the wall between the proximal 46 and distal 48 ends. Alternatively, the projections 64 may be in the form of one or more annular ring(s) or a tubular structure that encircles or substantially surrounds the external surface 52 of the lumen 50. As FIGS. 7 and 8 illustrate, the multiple projections 64 comprise a series of generally T-shaped wings that extend from the external surface 52 of the lumen 50. The radially outward-most surface 66 of the protrusions (i.e. the top portion of the "T" shape in FIG. 8) preferably extends the longitudinal length of the vial, thus forming an outer vial surface generally at 68 having a relatively constant external diameter 70, although, it is also contemplated that the outward-most surface 66 of the protrusions 64 extend only partially along the length of the vial between the proximal 46 and distal ends 48, and, like the lumen 50, may also have a variable diameter that is more narrow at one end and wider at the other end, for example. The outermost surface 66 of the protrusions 64 may have a diameter of approximately 12 mm, and preferably the shape and/or diameter of the protrusions 64 is configured to allow the vial 18 to stand upright on a surface or be held securely in the rack or organizer 16 in the cryo bath 4. Alternatively, the multiple projections 64 comprise multiple walls that extend radially outwardly from the external surface 52 of the vial lumen 50. In one non-limiting example, and as shown in FIGS. 12 and 13, the projections comprise two center walls 136 and two end walls 138. The center walls 136 include flat, generally parallel surfaces, and the end walls 138 include an inner surface 140 that is generally parallel to the center walls 136 and an outermost surface of the end walls 142 preferably has a rounded surface. The radially outward-most surface of the projections preferably extend the length of the vial (or alternatively, extend only a portion of the length) thus forming an outer vial surface having a relatively constant external diameter and preferably having a shape that is configured to allow the vial 18, 126 to stand upright on a surface or be held securely in the rack 16 or cane 120 in the cryo bath 4, 112.

FIGS. 10, 11 and 13 illustrate a side cross-sectional view of a vessel or vial 18, 126 that may be used with the cryogenic storage device 2, 112 described herein, and, as shown there, vial 18, 126 is preferably constructed of a single integral piece of material, such as by injection molding or the like, although, the vial 18, 126 may also be constructed of separately formed or molded pieces that are secured together by adhesive, bonding and the like. An intermediate space 72, 144 is formed between the external surface 52 of the lumen 50 and a surface of the radially outwardly extending protrusions 64 such that air (or fluid in the event that the vial is submerged in a liquid or gas) can flow into the intermediate space 72, 144 and substantially surround the external lumen wall 52. Where the protrusions 64 are a series of T-shaped walls (FIGS. 7-11) extending from the lumen external surface 52 or a series of substantially parallel walls (FIGS. 12-13), air or fluid including liquid nitrogen 30 may enter the intermediate space 72, 144 from both the sides and the bottom of the vial by flowing through the spaces formed between the series of projections, including side slots 74 and bottom openings 76. Although both fluid and air can flow into the intermediate space 72, 144 and surround the external wall 52 of the lumen 50, preferably nothing in the intermediate space can flow or otherwise enter the lumen 50, as the lumen wall is preferably non-permeable and is devoid of any openings.

Near the open proximal end 46 of the vial 18, 126, the external surface 52 of the lumen 50 and a portion of the radially extending protrusions 64 merge or are otherwise securely bonded together to form a unitary thicker wall 78 near the proximal open end 46. The open end is preferably configured to receive and engage a closure member 80, 146 therein, as described in further detail below.

For example, as shown in FIGS. 7, 10 and 11, the vial 18 may include a closure member 80 that may be removably received by the proximal open end 46 of the vial 18. In one example, the closure member 80 comprises a proximal capping portion 82 that is configured to engage with the open end 46 of the vial 18. Preferably, the open end of the vial and the capping portion 82 include corresponding inter-engaging structures that allow the closure 80 to be secured to the vial open end. As FIG. 9 shows, the internal surface 54 of the lumen 50 includes a threaded portion 84, while the capping portion 82 of the closure 80 includes a corresponding threaded portion 86 such that the closure can be screwed into the open end of the vial and securely held in place therein. It is also contemplated that the open end of the vial may include threads on an external surface of the unitary thicker wall 78 for engagement with the capping portion 82 which may be alternately configured for being fitted over the top of the vial 18 rather than fitted within the lumen 50. Other corresponding engaging structures on the closure member 80 and on the vial 18, respectively, may also be suitable for securing the closure to the vial, such as structures configured for snap fit or inter-locking engagement.

Turning back now to FIGS. 7, 10 and 11, the capping portion 82 includes a grip or handle 88, illustrated generally as a loop or tab, but which may be any protruding surface or member to allow the user to grasp the proximal most end of the closure 80, insert the closure into the open end 46 of the vial, and secure the closure in place such as by twisting or screwing the closure until the threads 84, 86 (or other suitable engaging members) are tightly engaged.

The closure member 80 also preferably includes a sealing portion located just distal to the capping portion 82. As FIGS. 10 and 11 illustrate, a deformable sealing member 90, such as a plug or stopper is provided. The sealing member 90 includes an external surface 92, which is preferably tapered radially inwardly, such that it corresponds to the shape and taper of the internal lumen wall 54. In other words, the lumen 50 comprises a female taper, while the deformable sealing member 90 provides a correspondingly shaped male taper which tightly and securely engage each other, such as by friction fit. In fact, the external tapered surface 92 of the sealing member 90 may have a diameter that is slightly larger than the portion of the internal lumen wall 54 that it is intended to engage such that when the closure 80 is inserted into the lumen 50, the lumen internal surface 54 presses radially inwardly against the external surface 92 of the sealing member 90 to provide a leak-proof impermeable seal. Preferably, the seal created is impermeable to liquids and gasses, including liquid nitrogen, at a variety of temperatures that may range from −196 degrees C. to 37 degrees C.

In another example, as illustrated in FIGS. 12 and 13, the closure member 146 is removably received by the proximal open end 46 of the vial 126. In this example, the capping portion 82 and sealing portion 90 of FIGS. 7-11 are shown as a generally unitary structure 148. The closure member 146 has an outer surface 150 that extends above, and partially surrounds, the open end 46 of the vial. In this way, the outer surface 150 of the closure member 146 also serves as a grip and/or handle to allow the user to grasp for securing and removing the closure member 146. The sealing portion 148 of the closure member 146 includes an external surface 152 which is preferably tapered such that it corresponds to the shape and taper of the internal lumen surface 54. This provides for an interference fit between the external tapered surface 152 of the sealing member 148 and the internal surface 54 of the lumen near the open end 46 of the vial 126. Similar to the embodiment of FIGS. 7-10, the external tapered surface 152 of the sealing member 148 illustrated in FIGS. 12 and 13 may have a diameter that is slightly larger than the portion of the internal lumen wall 54 that it is intended to engage such that when the closure 146 is inserted into the lumen 50, the lumen internal surface 54 presses radially inwardly against the external surface 152 of the sealing member 148 to provide a leak-proof impermeable seal. Preferably, the seal created is impermeable to liquids and gasses, including liquid nitrogen, at a variety of temperatures that may range from −196 degrees C. to 37 degrees C.

As also illustrated in FIGS. 12 and 13, closure member 146 may include at least one opening or slot that is shaped to receive a corresponding structure, such as one or more ears 156 at the open proximal end 46 of the vial 126. As FIG. 12 best illustrates, the closure member 146 can be inserted over the open proximal end 46 of vial 126 so that the ears 156 are inserted into corresponding slots 154. As the user rotates the closure 146, the ears 156 slide into channel 158 (or into two opposing channels 158). As the closure 146 is rotated further, and ears 156 are slideably engaged with the channel 158, the angle of channel 158 forces the closure further downward so that sealing member 148 is pushed tightly into the vial lumen 50 and outer surface 152 tightly engages inner lumen wall 54 to ensure a secure leak-proof seal. When ears 156 are positioned at the end of channel 158, the closure member 146 is locked securely in place, such as occurs with a bayonet twist lock. It is also contemplated that other attachment and/or locking mechanisms may be used to securely attach the closure member 146 to the vial 126, such as friction fit, snap fit, corresponding threads, and the like.

The distal end portion 48 of the lumen 50 is configured to receive a biological sample therein. In one non-limiting example, the particular embodiment illustrated in FIG. 11 may find application in the cryopreservation of a semen sample 94 containing sperm cells, but may also be used for containing, preserving and/or storing a variety of biological samples. FIGS. 7, 10 and 13 illustrate another example of a vial 18, 126 which may find particular application in the vitrification of biological samples, including the vitrification of one or more embryos. As shown there, the closure member 80, 146 includes a capping portion 82 and a sealing member 90 (FIGS. 7-11) and a closure member 146 (FIGS. 12-13) as described above, and preferably further includes a stem 96 extending from the sealing member 90, 148. A trough or hook 98 is formed near the distal tip 100 of the stem 96 for holding and retaining a specimen, such as an embryo 160 suspended in a droplet of vitrification media. The embryo 160 may remain in the hook portion of the stem 96 during vitrification and storage in the vial 18, 126.

The vial 18, 126 and the closure 80, 146 are preferably constructed of the same material so as to ensure the same thermal contraction properties of the respective materials including but not limited to polypropylene, polyethylene, polycarbonate and/or COC (cyclic olefin copolymer), although it is also contemplated that any material that is biocompatible with the particular biological sample and suitable for cryopreservation and/or vitrification may be used. Alternatively, the vial 18, 126 and closure 80, 146 may be constructed of different materials having the same or substantially similar thermal and mechanical properties. Thus, as the vial 18, 126 (containing a biological sample and sealed with the closure member) is subjected to the extreme temperature changes and high cooling rates required for proper cryopreservation and/or vitrification, the sealing member 90, 148 and internal lumen surface 54 maintain a tight and secure sealing engagement so as to isolate the sample receiving chamber 60 near the distal end portion 48 of the lumen (and any sample held therein) from the external environment while also preventing inadvertent leakage or seepage of gasses or liquids (including liquid nitrogen) into the sample chamber 60 of the lumen 50, even as the sealed vial 18, 126 is submerged in and/or subjected to long term storage in liquid nitrogen. In other words, a "closed system" within the vial lumen may be created and maintained for sealed storage of a sample in a variety of environments and temperature ranges, including during vitrification and storage in liquid nitrogen, without the need for providing additional or supplemental sealing measures to protect the samples during storage and/or to prevent liquid nitrogen from penetrating into the specimen-retaining chamber 60 of the vial.

However, it is not essential that the vial include an impermeable seal or otherwise provide a "closed system" for the biological sample being held therein as described above. It is also contemplated that the vial 18, 126 may include a variety of closure or capping members that may cover the open end 46 of the vial but that do not create any particular type of seal or, alternatively, the vial may not necessarily include a closure member. It is also contemplated that a variety of vessels or vials may be used with the bath described herein. For example, other commercially available containers, tubes, vessels, vials, straws and the like may be used to contain a particular biological specimen during cryopreservation and/or vitrification, as will be appreciated by one of skill in the art. Selection of a particular vessel may be based on a variety of factors including, but not limited to, the specific biological specimen being handled, the procedure being carried out and/or the desired outcome or objective.

Figure 4:
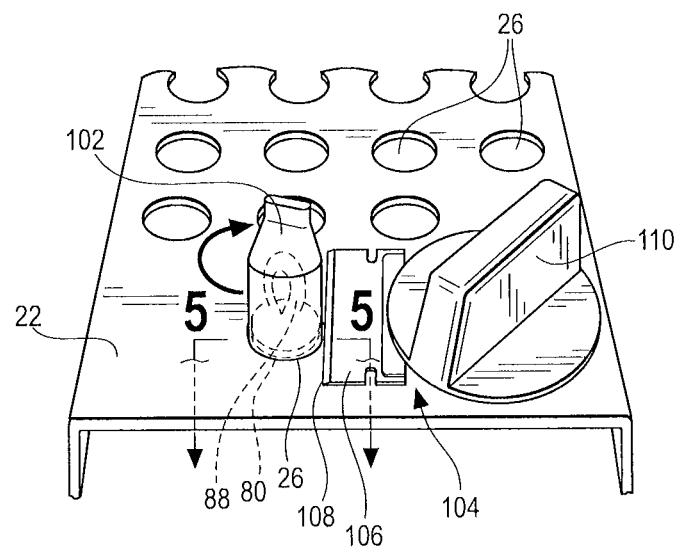
FIG. 4 is a perspective view of one example of a cutting element that may be associated with a cryogenic storage device, and more particularly, a cutting element mounted to a rack or organizer portion of a cryogenic storage device for holding and organizing one or more vessels containing a biological sample.
Figure 5:
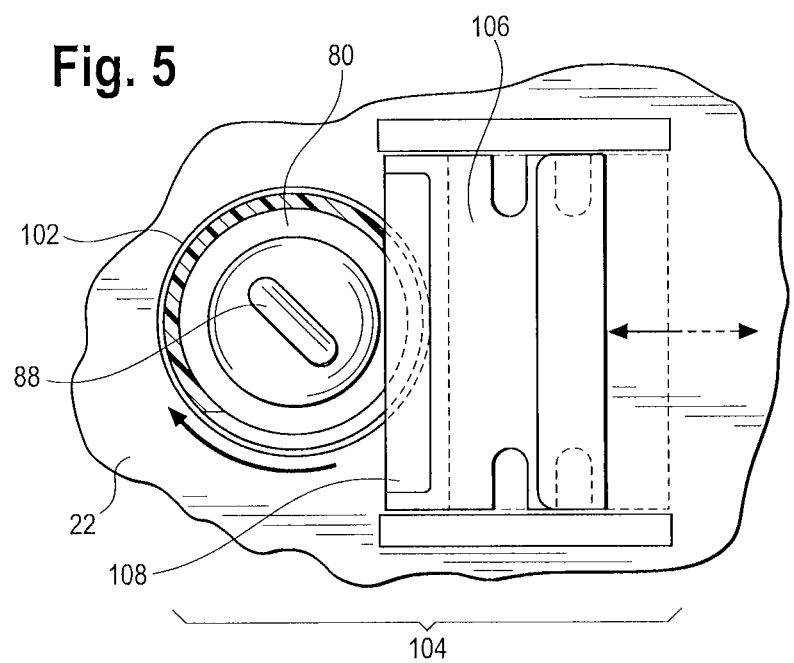
FIG. 5 is a top view of one example of a cutting element that may be used or associated with the cryogenic storage device described herein.
Figure 6:
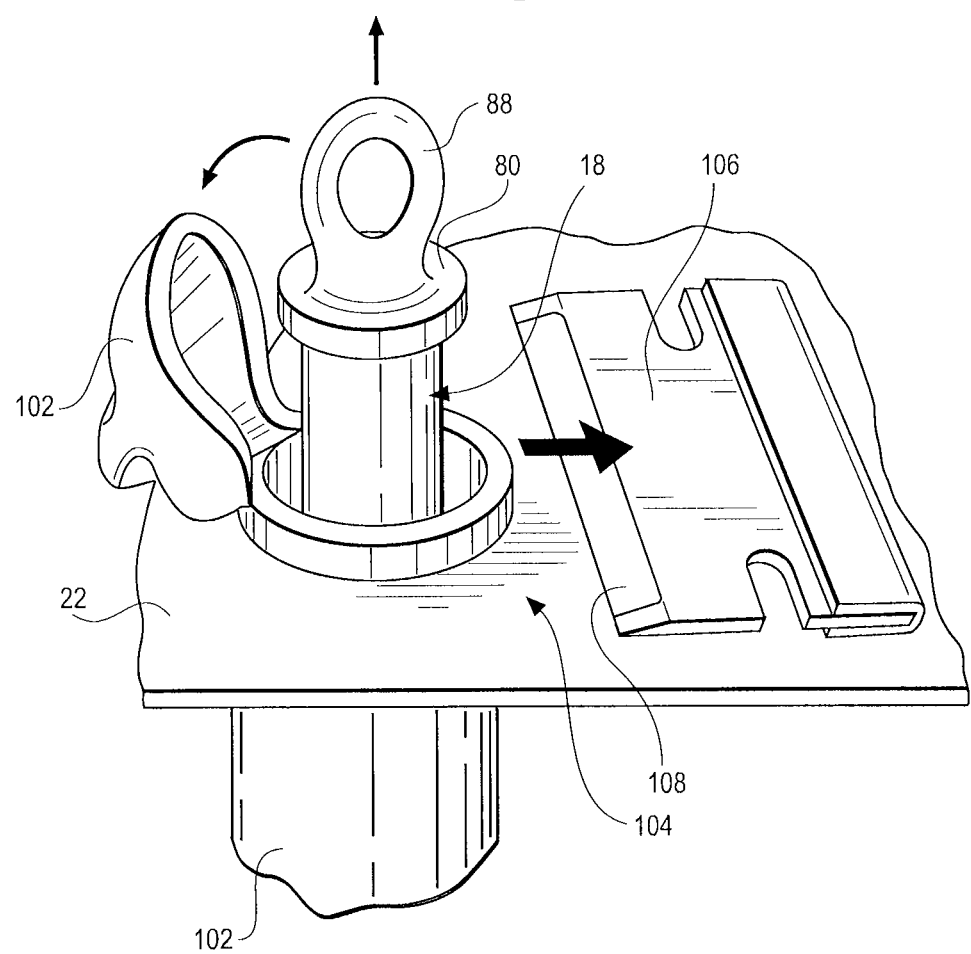
FIG. 6 is a perspective view of one example of a cutting element slicing an outer sleeve or overwrap that encased biological sample-containing vessel as the vessel is held in an organizer or rack within the storage device.

In yet another example, the selected vessel, including but not necessarily limited to vial 18, 126 may be sealed or covered by an additional sealing means. More particularly, in the event that a particular vial 18, 126 does not provide a sealing closure as needed or desired by the user, an additional sealing means, such as a sleeve, cover 102 or similar overwrap, may be provided as shown in FIGS. 4-6. The vial 18, 126 may be encased or enclosed by the sleeve 102, such as by heat-sealing the sleeve over the vial, to provide a more secure or impermeable seal or otherwise isolate the biological sample held in the vial and prevent exposure, contamination or leakage into the vial from the external environment.

In the event that the vial is enclosed or encased in a sleeve or overwrap 102, it may be desirable to provide a device that includes a cutting element 104 or member for cutting, opening and/or otherwise assisting the user in removing the sleeve 102 from the outside of the vial 18, 126 when desired. An example of one such cutting element 104 is shown in FIGS. 4-6. As illustrated there, the cutting element 104 may include a blade 106 that is mounted on the top portion 22 of the vial rack 16 or cane 120. The blade 106 includes at least one sharpened or cutting surface 108. Preferably, the cutting element is moveable towards (or alternatively, at least partially circumferentially around) one or more of the apertures 26 formed in the rack 16 (or apertures 124 in cane 120) where a vial 18, 126 may be received and held. For example, the blade 106 may include a handle 110 or other gripping surface that allows the user to move the blade in a direction towards a vial held in the rack as shown in FIGS. 5 and 6 so that the cutting surface 108 of the blade 106 contacts a sleeve 102 or overwrap that encases the vial. By moving or rotating the blade 106 and/or moving or rotating the vial 18, 126 the cutting surface 108 of the blade may slice and cut the sleeve 102, thus exposing the vial 18, 126 that was once encased therein. The user may continue to use the blade 106 to cut the sleeve 102 or may manually grasp the now loosened flap of the sleeve 102 that has been cut by the blade as shown in FIG. 6, peel the sleeve away and remove the vial from within the sleeve. The biological sample held within the vial 18, 126 may then be accessed and retrieved, such as for thawing and use or further treatment of the sample.

In addition to the above described example, it is contemplated that the cutting element may also include a variety of other configurations or designs that are suitable for slicing, cutting or otherwise facilitating removal of the sleeve 102 from the vial. For example, the cutting element may be similar to a "cigar cutter" with one or more circular, curved or semi-circular blades located adjacent to the vial 18, 126 which may be used to cut the sleeve 102. A portion of sleeve 102 may be inserted between circular or curved or alternatively shaped blades or cutting elements that are located on each side of the vial, and when the blades are moved towards each other, the sleeve can be cut.

The above-described device may be used for cryopreservation and vitrification of a biological sample in accordance with the following exemplary methods. First, a cryo bath 4, 112, as described above may be provided and filled with a desired volume of cryogenic freezing medium 30 such as liquid nitrogen. Further, a biological sample may be placed directly into the lumen 50 of a vessel or vial 18, 126. More particularly, any type of liquid sample, including but not limited to a semen sample 94 containing sperm cells, may be introduced into the distal sample-receiving portion 60 of the vial lumen 50 as best shown in FIG. 11. Alternatively, an embryo 160 suspended in a droplet of vitrification media may be loaded or deposited by known and acceptable techniques onto the hook 98 located near the distal tip 100 of the stem 96 that extends from the closure member 80, 146.

The user may then secure the closure member 80 in place in the proximal open end 46, such as by screwing the capping portion 82 or closure 146 into the vial. The corresponding engaging members on the vial 18, 126 and capping portion 82 such as the threads 84, 86, (or the bayonet twist lock of FIGS. 12-13 with corresponding engaging ears 156 and channels 158) allow the closure member 80, 146 to be securely held in place and also provide a signal to the user that the closure member has been sufficiently screwed into the open end 46 when resistance is felt as the closure is being twisted into place.

The biological sample held in the distal end 48 of the lumen 50 is thereby closed from the external environment and is ready for cryopreservation and/or vitrification and storage in the bath 4, 112.

The vial 18, 126 may be cooled by exposure to any suitable cryogenic freezing medium 30, and preferably, by submerging at least a portion of the vial 18, 126 into a volume of liquid nitrogen in the bath 4, 112. For example, the vial may be arranged onto the rack 16 or cane 120 in the bath of liquid nitrogen 30 in order to cool the biological sample within the vial lumen 50 to a suitable temperature. In a cryobanking facility, for example, a semen sample 94 may be cryopreserved, or alternatively, an embryo 160 may be vitrified, in accordance with these exemplary methods in order to maintain the viability of individual sperm cells or of the embryo, which may be later thawed and used in various assisted reproduction applications.

In another example, depending on the particular procedure being performed, it may be desirable or necessary to prepare the vial 18, 126 for receiving and vitrifying a biological specimen that has been loaded onto the stem tip 96. Such preparation of the vial may include, for example, pre-cooling the vial 18, 126 in the bath of liquid nitrogen 30 before the biological sample is introduced into the vial lumen 50. The user may place the empty vial 18, 126 onto the rack 16 or cane 120 such that at least the distal end 48 of the vial is submerged in the pool of liquid nitrogen 30 underneath. The liquid nitrogen may flow around the vial and into and between the radially outwardly extending projections 64 to fill the intermediate space 72, 144 and surround the lumen wall. In this way, the lumen interior may be cooled by thermal transfer as external surface 52 of the lumen 50 is exposed to the liquid nitrogen 30 flowing in the intermediate space 72, 144. As a result, the internal lumen of the vial becomes a region of cold air, having a temperature suitable for vitrifying a sample that is introduced into the sample-receiving portion 60 of the lumen 50. One or more vials 18, 126 may be "pre-cooled" in this way such that the vials are sufficiently prepared for receiving and vitrifying a sample and having the internal lumen 50 at thermal equilibrium. With one or more vials 18, 126 ready and waiting in a pre-cooled condition, the closure member 80, 146 having an embryo 160 (or other sample) retained on the tip 100 of the stem 96 that extends from the vial cap 82, can be inserted into the lumen 50. Once the distal tip 100 of the stem, holding an embryonic sample thereon, has been inserted into the lumen 50 and is properly positioned within the sample-receiving portion 60 at tapered distal end 48, the user may then secure the closure member 80, 146 in place such as by screwing the capping portion 82 into the open end 46 of vial in a manner similar to that already described above. The region of cold air within the lumen created by the liquid nitrogen (or other suitable cooling medium 30) surrounding the lumen wall provides the proper temperature and environment in the lumen, in the order of 1,000 degrees C./minute, for example, to vitrify the sample held on the stem tip 100 without liquid nitrogen contact. The vitrified sample within the vial 18, 126 may be retained on the rack 16 or cane 120 for storage in the bath 4, 112 by known and acceptable methods, including storage in liquid nitrogen.

In one example, the seal provided between the capping member 82, 148 and the vial lumen 50 is impermeable and isolates the biological sample in the vial lumen from the external environment and may be stored directly in the liquid nitrogen bath. Alternatively, the vial 18, 126 or other type of vessel containing the biological sample therein may be additionally sealed or enclosed within a sleeve 102, cover or overwrap before being placed on a rack 16 or cane 120 and stored in the bath of liquid nitrogen 30.

In another example, barcodes or other labeling or identification tags or markers (not shown) can be included on the individual vials 18, 126 and/or on the rack 16 or cane 120 or elsewhere on the bath 4, 112 in order to identify the biological specimens in a way that is compatible with established laboratory barcode archiving or identification systems. The vials 18, 126 may also be provided in a variety of colors or styles in order to assist in the identification and archiving process.

The above-described cryogenic storage device 2, 112 may be sold and/or provided to healthcare providers and physicians either alone or in the form of a kit or packaged set. In one example, such a kit may preferably include a cryo bath 4, 112 as described herein as well as a vessel, vial or container, such as but not limited to the vial 18, 126 described herein for receiving and retaining a biological sample during cryopreservation, vitrification and/or storage in the bath 4. Of course, the kit may also contain more or fewer items, components and tools than those previously described as required or necessary for the particular procedure being performed.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A cryogenic storage device comprising:
a container comprising a bottom wall portion and at least two side wall portions, the bottom and side wall portions forming an interior chamber and wherein the container comprises an inner surface and an outer surface,
a thermal insulating material covering at least a portion of one or both of the inner and outer surfaces of the container;
a first member having a surface extending generally vertically from the bottom wall portion of the container and dividing the interior chamber into a first sub-chamber adapted for receiving a volume of cryogenic freezing medium and a second sub-chamber;
a second member having a surface extending generally horizontally between the sidewall portions of the container into the first sub-chamber, wherein the generally horizontal surface comprises at least one opening formed therein configured to receive one or more biological sample-containing vessels.

2. The device of claim 1 wherein the container comprises a generally bowl-shaped reservoir or bath.

3. The device of claim 1 wherein the container comprises plastic or metal.

4. The device of claim 1 wherein the insulating material comprises at least one of polystyrene foam and a vacuum insulation layer.

5. The device of claim 1 wherein the cryogenic freezing medium comprises liquid nitrogen.

6. The device of claim 1 wherein the generally vertical surface of the first member comprises at least one of a wall, a plate, a sheet, a membrane and a barrier.

7. The device of claim 1 wherein the generally horizontal surface of the second member comprises at least one of a plate, a rack, a cane, a support, a holder, an organizer and a shelf.

8. The device of claim 1 wherein at least one of the first and second members is integrally formed with the container.

9. The device of claim 1 wherein at least one of the first and second members may be secured to the container by at least one of interference fit, friction fit, welding, adhesive, bonding and a fastener.

10. The device of claim 1 wherein the at least two sidewall portions comprise at least one groove formed therein and wherein at least a portion of the second member is configured to be received within the at least one groove.

11. The device of claim 1 wherein the biological sample-containing vessel comprises a vial adapted for the cryopreservation of a biological sample therein.

12. The device of claim 1 wherein the second sub-chamber comprises an overflow chamber configured to receive a volume of cryogenic freezing medium from the first sub-chamber.

13. The device of claim 1 wherein the first member further comprises a top surface configured to allow cryogenic freezing medium to flow from the first sub-chamber to the second sub-chamber and wherein the top surface is located at a selected vertical position in order to maintain a volume of liquid nitrogen in the first sub-chamber at a desired level.

14. The device of claim 1 further comprising a cutting element.

15. A cryogenic storage kit comprising:
a. a cryogenic storage device comprising:
a container comprising a bottom wall portion and at least two side wall portions, the bottom and side wall portions forming an interior chamber and wherein the container comprises an inner surface and an outer surface,
a thermal insulating material covering at least a portion of one or both of the inner and outer surfaces of the container;
a first member having a surface extending generally vertically from the bottom wall portion of the container and dividing the interior chamber into a first sub-chamber adapted for receiving a volume of cryogenic freezing medium and a second sub-chamber;
a second member having a surface extending generally horizontally between the sidewall portions of the container into the first sub-chamber, wherein the generally horizontal surface comprises at least one opening formed therein configured to receive one or more biological sample-containing vessels;
b. a vessel adapted to receive and retain a biological sample during cryopreservation.

16. The kit of claim 15 wherein the container further comprises a generally bowl-shaped reservoir or bath.

17. The kit of claim 15 wherein the insulating material comprises at least one of polystyrene foam and a vacuum insulation layer.

18. The kit of claim 15 wherein the generally vertical surface of the first member comprises at least one of a wall, a plate, a sheet, a membrane and a barrier.

19. The kit of claim 15 wherein the generally horizontal surface of the second member comprises at least one of a plate, a rack, a cane, a support, a holder, an organizer and a shelf.

20. The kit of claim 15 wherein at least one of the first and second members may be integrally formed with the container.

21. The kit of claim 15 wherein the vessel comprises at least one of a container, a tube, a vial, a straw and an ampule.

22. The kit of claim 15 wherein the second sub-chamber comprises an overflow chamber configured to receive a volume of cryogenic freezing medium from the first sub-chamber.

23. The kit of claim 15 wherein the vessel comprises:
a body comprising a proximal open end and a sealed distal end and a variable diameter lumen extending there between,
the lumen having an external surface and an internal surface, the internal surface tapering generally radially inwardly from the proximal open end to the distal end and forming a sealing portion and a sample receiving portion,
a closure configured for removable attachment to the body wherein the closure comprises a capping member adapted for engagement with the proximal open end and a deformable member having a tapered external surface configured for sealing engagement with the lumen internal surface, and
at least two projections extending radially outwardly from the external surface of the lumen, the projections comprising a radially outward most surface extending between the proximal open end and the sealed distal end of the body.

24. The kit of claim 23 wherein the vessel further comprises at least one ear extending outwardly from the body adjacent the proximal open end and wherein the closure further comprises at least one slot that is configured to receive the at least one ear therein, such that when the closure is rotated the at least one ear is slideably engaged within the at least one slot and wherein the external surface of the deformable member comprises a male taper and the internal surface of the lumen comprises a female taper and wherein the male taper and female taper have corresponding taper angles such that a fluid tight seal is established between the respective tapered surfaces.

25. A cryogenic storage method comprising:
  a. introducing a biological sample into the lumen of a storage vessel;
  b. placing the storage vessel in a cryogenic storage device, the storage device comprising:
    i. a container comprising a bottom wall portion and at least two side wall portions, the bottom and side wall portions forming an interior chamber and wherein the container comprises an inner surface and an outer surface,
    ii. a thermal insulating material covering at least a portion of one or both of the inner and outer surfaces of the container,
    iii. a first member having a surface extending generally vertically from the bottom wall portion of the container and dividing the interior chamber into a first sub-chamber containing a volume of cryogenic freezing medium and a second sub-chamber;
    iv. a second member having a surface extending generally horizontally between the sidewall portions of the container into the first sub-chamber, wherein the generally horizontal surface comprises at least one opening formed therein configured to receive one or more biological sample-containing storage vessels;
  c. exposing at least a portion of the sample-containing vessel to a cryogenic freezing medium in the storage device.

26. The method of claim 25 wherein the lumen of the vessel is pre-cooled in the storage device to a temperature suitable for the vitrification of a biological sample in the vessel lumen prior to the step of introducing the biological sample into the lumen.

\* \* \* \* \*